United States Patent [19]

Hunter et al.

[11] 4,151,202

[45] Apr. 24, 1979

[54] PREPARATION OF DIALLYL DIMETHYL AMMONIUM CHLORIDE AND POLYDIALLYL DIMETHYL AMMONIUM CHLORIDE

[75] Inventors: Wood E. Hunter, Memphis, Tenn.; Theodore P. Sieder, Sauk Village, Ill.

[73] Assignee: Nalco Chemical Company, Oak Brook, Ill.

[21] Appl. No.: 934,923

[22] Filed: Aug. 18, 1978

Related U.S. Application Data

[60] Division of Ser. No. 833,113, Sep. 14, 1977, abandoned, which is a continuation-in-part of Ser. No. 763,469, Jan. 28, 1977, abandoned, which is a continuation-in-part of Ser. No. 662,397, Mar. 1, 1976, abandoned.

[51] Int. Cl.$^2$ ................ C07C 85/04; C08L 39/00
[52] U.S. Cl. ..................... 260/567.6 R; 260/29.7 H; 260/652 P; 526/295; 526/310
[58] Field of Search ............ 260/567.6 P, 29.7 H, 260/2 R

[56] References Cited

U.S. PATENT DOCUMENTS

| | | | |
|---|---|---|---|
| 2,923,701 | 2/1960 | Schuller et al. | 526/291 |
| 2,926,161 | 2/1960 | Butler et al. | 526/15 |
| 3,288,770 | 11/1960 | Buttler | 526/212 |
| 3,461,163 | 8/1969 | Boothe | 260/567.6 P |
| 3,544,318 | 12/1970 | Booth et al. | 196/1.5 |

*Primary Examiner*—James H. Reamer
*Attorney, Agent, or Firm*—John G. Premo; Robert A. Miller

[57] ABSTRACT

Water-soluble polymers of diallyl dimethyl ammonium chloride can be prepared from monomer solution containing a large amount of an alkali metal halide salt. Additionally, a method is disclosed for making high quality monomer which involves purification of allyl chloride which is used to prepare the starting monomeric material, optimum temperature control during caustic addition, and partial distillation to remove harmful impurities.

5 Claims, No Drawings

PREPARATION OF DIALLYL DIMETHYL AMMONIUM CHLORIDE AND POLYDIALLYL DIMETHYL AMMONIUM CHLORIDE

This is a division of copending application Ser. No. 833,113 filed Sept. 14, 1977, now abandoned which in turn is a continuation-in-part of copending Ser. No. 763,469 filed Jan. 28, 1977, now abandoned, which in turn is a continuation-in-part of copending Ser. No. 662,397 filed Mar. 1, 1976, now abandoned.

Polymers of diallyldimethylammonium halides are used in a variety of applications. These water soluble polymers can be used as flocculants for water and sewage treatment and other applications where a high molecular weight cationic polymer is needed. U.S. Pat. Nos. 2,926,161 and 3,288,770 discloses the polymerization of diallyldimethylammonium halide type monomers. However due to economic considerations with these processes and due to problems in obtaining high purity monomers, the realization of these references have not been completely achieved. U.S. Pat. No. 3,461,163 discloses the preparation of diallyldimethylammonium chloride (hereinafter referred to as DADMAC), a representative monomer of this group. By the use of processes similar to the one which we prefer to use in our invention, large amounts of alkali metal halide salts are formed. These salts are difficult to remove and care has been taken in the past to remove this salt formed from the monomer mixture. This salt removal process has increased the cost of the resultant monomer and as a result, has raised the cost of the finished polymeric material.

Another problem which has been studied by the prior art is that high quality monomer is difficult to obtain. Causes include the fact that the allyl chloride starting material used in the preparation of DADMAC monomer has been impure. This material is purified by most suppliers by an aqueous wash to give a water-washed grade. This material is generally shipped in carbon steel containers. Since the allyl chloride is saturated with water from washing, any decrease in temperature will result in water coming out of the solution. Slow hydrolysis of the allyl chloride then produces among other components allyl alcohol, diallyl ether and HCL. Hydrochloric acid present in the aqueous phase attacks the metal drum and deposits metal salts in the allyl chloride. The use of lined drums for use in the shipment of allyl chloride causes excess hydrochloric acid build up due to the fact that it cannot form iron salts, and thus further hydrolysis with this auto-catalytic process results in considerably larger amounts of the alcohol and ether. We have found that by purifying the allyl chloride prior to preparation of DADMAC monomer followed by synthesizing the monomer using improved techniques and then directly polymerizing the monomer solution so formed without the need for salt removal, a superior polymeric product is produced.

OBJECTS

It is, therefore, an object of our invention to provide to the art a method for the purification of allyl chloride.

A further object of our invention is to provide to the art an improved method for the preparation of diallyldimethylammonium halide monomer with the use of purified allyl chloride.

A still further object of our invention is to provide to the art a method for the preparation of homogeneous solution polymers of DADMAC from a DADMAC monomer solution containing salt.

Other objects will appear hereinafter.

THE INVENTION

In order to fully understand our invention, it will be necessary to break it up into two parts. The first of these parts is the synthesis of DADMAC.

PREPARATION OF THE MONOMER

As stated earlier serious problems have existed regarding the purification of allyl chloride used to produce DADMAC. Attempts have been made to distill the allyl chloride obtained commercially; however, this results in a loss of approximately 10% of the material as distillate bottoms and is very expensive. We have also found that by the use of a water washing technique which is preceeded by filtering the crude material, allyl chloride of sufficiently high purity is prepared which can be used to prepare high quality DADMAC. The method which we generally follow for purifying the allyl chloride encompasses the steps of:

A. Filtering a supply of allyl chloride;
B. Admixing said filtered supply of allyl chloride with water in a mole ratio of allyl chloride to water of from 5.0:1.0 to 1.0:5.0;
C. Allowing the mixture to settle, forming an organic allyl chloride phase, an aqueous water phase, and a rag phase;
D. Removing from the mixture the aqueous water phase;
E. Continuing steps B, C and D until the rag phase is less than 0.4% by weight of the allyl chloride started with;
F. Removing from the mixture the rag phase; and then,
G. Recovering a purified allyl chloride The crude supply of allyl chloride is filtered prior to washing with water so as to remove any insoluble iron salts which may decrease initiator efficiency or be active chain-transfer agents.

The filtration step may be performed by any number of methods and th mechanics of this filtration will be readily apparent to those skilled in the art. However, for the filtration of the crude allyl chloride, we prefer to use an in-line filter so as to minimize the volatility of this material. The pore size of the filter through which the allyl chloride is passed may vary but should be sufficiently small to retain all of the parriculate matter which may be present in the crude material. As an industrial practicality, however, the pore size of the filter selected must be large enough to allow a rapid passage of the allyl chloride; and as a result, we have found that an in-line filter cartridge having an approximate pore size of 10 microns will perform satisfactorily. It is to be understood, however, that it is within the scope of this invention to use filters having both large and small pore sizes so long as the particulate matter present in the crude material is removed.

With the filtration step of our invention, we have found that the rag phase obtained by water washing is reduced although this rag phase can also be reduced by further washing with water.

After the allyl chloride has been filtered it is then washed with water. Generally, the allyl chloride is mixed with a water in mole ratio of allyl chloride to water of from 5.0:1.0 to 1.0:5.0. Water soluble impurities such as allyl alcohol and other contaminates are removed from the allyl chloride by this step. The allyl chloride may be washed any number of times; however using commercially available materials with the filtration step of our invention, it is generally necessary to only contact the allyl chloride with the water once. It is also been found that when the allyl chloride is washed with water, a rag phase will generally form. This rag or emulsion will tend to be much smaller when the allyl chloride used has been filtered. Generally, the rag phase will be less than 0.4% by weight than the allyl chloride started with.

Since water washing of organic chemicals is well known in the art, it is unnecessary to go into detail since it will be apparent to those skilled in the art. It is sufficient to say that the water and allyl chloride should be mixed well, allowed to settle, and then separated. The water from the wash may be discarded.

Additionally, it is sometimes advisable, although not necessary within the scope of our invention, to add to the water used to wash the allyl chloride from 1.0-50,000 ppm of an alkali metal carbonate and preferably from 5-10,000 ppm of this type of material. A still further refinement of the above process involves the addition of from 1-10,000 ppm of a sequestration agent such as the sodium salt of ethylenediaminetetracetic acid or any well known chelating agent. It should be emphasized, however, that the use of an alkali metal carbonate or sequestration agent is not necessary but may on some occasions tend to improve the quality of the resultant purified allyl chloride.

One of the great advantages of our process is that generally less than 0.4% by weight of the allyl chloride is lost compared to 10% and upward with conventional distillation techniques. This involves a savings of both fuel and process time as well as, of course, an increased yield of purified allyl chloride. Additionally, it is sometimes expedient to keep the allyl chloride due to its volatility and reactivity under a blanket of inert gas during the washing step. This is in many ways a safety precaution to avoid any chance of oxidation.

After the purified allyl chloride is obtained, it is reacted with dimethylamine and neutralized with an alkali metal hydroxide, generally sodium hydroxide. A synthesis of this type is described in U.S. Pat. No. 3,461,163 which is hereinafter incorporated by reference. The synthesis of DADMAC monomer is generally well known and need not be elaborated on here with the possible exception that:

(1) It should be pointed out that the purity of the allyl chloride used is essential to the preparation of good DADMAC monomer. Impurities which include iron and water soluble organics are removed by the aqueous wash and filtration step of our invention.

We have found by the use of the filtration step encompassed by our invention that the number of times the allyl chloride must be washed to obtain material of sufficient purity can be reduced. With the use of our invention, it is generally only necessary to wash the allyl chloride one time. It is also noted that the filtration step employed will reduce the amount of rag phase formed during the subsequent washing step(s). This results in a large savings of both time and materials to produce an allyl chloride which is satisfactory for use in the preparation of a pure DADMAC monomer.

(2) As was pointed out in U.S. Pat. No. 3,461,163, pH control during the preparation of DADMAC monomer is essential. We have found that the control of pH as well as temperature prevents allyl alcohol and allyl dimethylamine contaminates from forming.

The control of pH and temperature prevents allyl alcohol and allyl dimethylamine, both contaminates, from forming. The use of a temperature of 50°-65° C. is preferred, and we have found that higher temperatures (i.e. greater than 65°) aid in the formation of impurities. With temperatures lower than 45° C., the reaction is sluggish and impurities also tend to form. As to pH control, slow addition of the alkali metal hydroxide, usually sodium hydroxide, is preferred to prevent high concentrations of allyl alcohol from forming.

By the use of our process, the pH does not have to be carefully monitored due to the slow rate of caustic addition and temperature control.

(3) After the DADMAC monomer is formed, excess allyl chloride is stripped according to our invention from the solution and additional amounts of water are removed to sufficiently remove allyl alcohol and allyl dimethylamine which distill with the water to less than 0.01% level by weight. We have fund that it is extremely important to remove any unreacted allyl alcohol due to the fact that this material as present may act as a change transfer agent during the preparation of the polymer.

(4) We have also found tht an important improvement in our invention is the elimination of the filtration step to remove alkali metal salts produced during the neutralization. Since the polymerization step of our invention can be carried out with the salt present, there is no need to remove this salt; and preferably, it is left in the final monomer solution. This eliminates a costly and time consuming filtration step, and we have found surprisingly that the alkali metal halide salt does not interfere with the polymerization of the DADMAC. The resulting monomer solution after neutralization will generally contain 25-50% by weight of the DADMAC monomer and 9-20% by weight of suspended water soluble alkali metal halide salt.

From the reaction scheme above for the preparation of DADMAC, it will be seen that for each mole of DADMAC prepared, one mole of an alkali metal halide salt will be prepared. Since DADMAC has an approximate molecular weight of 161.5, and for example with sodium chloride which has a molecular weight of 58.5, it will be seen that for each 100 grams of DADMAC prepared, 36.2 grams of sodium chloride will be formed. Thus, generally but depending on the exact neutralization practice, with the use of sodium hydroxide, 36.2% by weight sodium chloride will be prepared based on the weight of DADMAC prepared. This figure will vary, of course, when other alkalizing agents are used, but is generally illustrative of the quantity of salt formed during the reaction.

The Solution Homopolymerization of Diallyldimethylammonium Chloride

The method which we have employed to polymerize the solutions of DADMAC produced which are described above generally encompass the steps of:

A. Purging said monomer solution;
B. Heating said monomer solution to a temperature of 120°-180° F.;
C. Adding to said monomer solution a free radical catalyst;
D. Polymerizing said monomer solution under free radical forming conditions so as to prepare a polymer of DADMAC in an aqueous solution;

E. Cooling said polymer in aqueous solution while adding water as necessary to solubilize any of said dalt contained in said solution;

and stil more specifically described by steps of:

A. Purging said monomer solution with an inert gas;
B. Adding to the monomer solution from 0.015–0.05% by weight of a chelating agent based on the weight of DADMAC present in said monomer solution while maintaining a flow of inert gas;
C. Heating said monomer solution with agitation to a temperature of 130°–140° F.;
D. Adding to the monomer solution from 0.75–5.0% by weight, based on the weight of DADMAC of an inorganic free radical initiator;
E. Maintaining the temperature at 135°–145° F. by applying a vacuum, so as to allow said solution to boil while adding to the solution water to replace that distilled;
F. Heating said solution to 170°–180° F.;
G. Adding from 0.50–2.50% by weight of an inorganic free radical initiator based on the weight of the DADMAC;
H. Maintaining the temperature of step F for a sufficient period to insure the complete reaction of the DADMAC under vacuum while continuously replacing distillate with fresh water;
I. Cooling the resultant solution, and diluting said solution with water to a point where all of said alkali metal halide salt is soluble; and then,
J. Recovering a solution homopolymer of DADMAC containing 15–30.0% by weight polymer and from 4–12% by weight water soluble alkali metal halide salt.

The above procedure produces a reproduceable solution polymer having an intrinisic viscosity in 1.0 N sodium nitrate of from 0.25 to 0.8 and preferably from 0.25–0.60. While basically this is a conventional free radical polymerization, we have found that the monomer solution employed may contain large amounts of salts. As seen for example U.S. Pat. No. 3,288,770 and specifically in the examples that are shown, the monomer was precipitated and purified which is not necessary for the instant invention.

the chelating agent in the use of our invention is generally an alkali metal salt of ethylenediaminetetraacetic acid. The preferred alkali metal is sodium. While this chelating agent is preferred, it will be readily seen by those skilled in the art that other materials can be readily used and will accomplish the same purpose. It is believed that this material ties up trace amounts of iron or other metallic impurities which may destroy the initiator, thus preventing polymerization.

Catalysts useful for the preparation of our polymers include conventional redox peroxide, and other free radical catalysts which will peform within the scope of our invention. Alkali metal or ammonium persulfates are preferred due to their solubility, reactivity in the aqueous monomer, and the produceability of polymer obtained. The preferred ctalyst is ammonium persulfate.

The catalyst of our invention is generally used at a level of from 0.5 to 7.50 by weight of DADMAC present. It will be seen, however, that it is often times advisable to divide the necessary catalyst into two separate charges so that after a first period of heating and polymerizing, more catalysts can be added; and with continued heating, the polymerization can be delivered farther to completion. In the preferred mode of our invention from 1.25 to 2.76% by weight of initiator is used. This is generally divided into two charges using as a first charge 0.75 to 5.0% by weight and as a second charge 0.50–2.50% by weight based on the weight of DADMAC.

While not removing the salt limits the final concentration of the polymer which can be produced due to the dilution necessary to dissolve the alkali metal halide, usually sodium chloride, at the end of the reaction, it will be seen that the dilution employed is not detrimental due to the fact that at the higher temperatures of polymerization, the polymer has a much lower viscosity, and upon lowering the temperature, viscosity increases to a point where the polymer becomes extremely difficult if not impossible to handle. By the end dilution a product containing dissolved salt at a viscosity which can be handled is prepared. The final polymer containing 15–30% by weight polymer and only from 4–12.0% by weight salt, has a viscosity where it can be readily handled while still not prohibiting shipping or other transfer of the material economically.

While the above polymerization step has been referred to as a solution polymerization, it is to be noted that the salt within the reaction is not soluble but does not effect the quality of the polymer so produced. This salt is for all practical purposes suspended in the poly-DADMAC solution. Another important factor in the use of our invention is the isothermal nature of the polymerization to achieve the highest molecular weight product. This is conveniently done in small scale equipment with water cooling but in larger vessels, vacuum control is preferred.

In order to illustrate our invention the following examples are presented:

EXAMPLE I

This example will illustrate the purification of allyl chloride prior to preparing DADMAC monomer. To a 50 gallon reactor equipped with temperature sensing device, bottom outlet, top inlet, agitator, and distillation equipment was charged 104 pounds of a commercially available supply of allyl chloride. To this was added 31.5 pounds of water. After adding the water, the reactor was purged with nitrogen until a pressure of 15 pounds per square inch was reached. The pressure was then lowered to 3 pounds per square inch. Agitation was then started, and was continued for ½ hour at which time agitation was stopped. The resulting phases were allowed to settle for ½ hour at which time the bottom aqueous layer was drained off. If a large amount (greater than 0.1 pound) of a reddish brown interface was noted, the above steps were repeated using fresh water. After purification, the resulting allyl chloride was held in the reactor for further use.

EXAMPLE II

The process of Example I was followed except that the allyl chloride used was filtered through a 10 micron filter cartridge prior to being added to the reactor.

EXAMPLE III

To the washed allyl chloride prepared in Example I was added 24.1 pounds of anhydrous dimethylamine over approximately 3½ hours. The temperature of the reactor during this time was allowed to raise to 120° F. at which time cooling was applied to hold the temperature between 120° to 130° F. After all of the dimethylamine had been added, the reactor was held at a temperature of 120°–130° F. for thirty minutes. 42.1 pounds of an aqueous solution containing 51% by weight sodium hydroxide was then added to the reactor over a period of 4½ hours. Cooling was used to maintain the temperature at 130°–140° F. After all of the sodium hydroxide had been added, the reactor was held at 130°–140° F. for thirty minutes. During the addition of sodium hydroxide the maximum pressure which developed was 30 pounds per square inch.

During caustic addition sodium chloride was formed and precipitated. The reactor was cooled to 100° F. and the reactor was vented to relieve excess pressure. The resulting monomeric solution was then heated to approximately 150° F. and approximately 20.5 pounds of allyl chloride was stripped off. This material was drained and saved for future use. The majority of the allyl chloride removed was distilled at a temperature of 113°–125° F.; however, the temperature was raised to 150° F. to remove as much of the allyl chloride as possible. One hundred pounds of water was then added to the reactor and 50 pounds of water, contaminated with impurities, was removed using a vacuum of approximately 120 millmilters of Hg at 140°–150° F.

After this material had been removed, the vacuum was broken by the addition of nitrogen to the vessel and the temperature was adjusted to 135° F. Crystalline sodium chloride was present in the mixture, and agitation was necessary to keep it suspended. This material was then held at this temperature in a reactor for further processing.

EXAMPLE IV

The procedure of Example III was followed using the allyl chloride prepared in Example II.

EXAMPLE V

To the material in the reactor prepared in Example III was charged a solution of 13 grams of the sodium salt of ethylenediamine tetraacetic acid in 2.5 pounds of water. The reactor was then purged with nitrogen and the temperature of the reactor was adjusted to 133°–137° F. A vacuum of 100 millimeters of mercury was then applied and a solution containing 472 grams of ammonium persulfate in 2.5 pounds of water was added. The reaction initiated within a few minutes, and temperature was controlled at 138°–142° F. by using whatever vacuum was necessary. Water removed by boiling in this fashion was not replaced directly, but for every pound of water removed a pound of fresh water was added.

During the polymerization the polymer salt slurry became very viscous, i.e. about 70,000 cps., at the reaction temperature. Vacuum boiling to control the temperature, however, was readily controlled and no foaming or other problems were noted. The temperature was held by vacuum control for approximately 3–5 hours. If in the event reaction subsides before 3 hours, a catalyst solution consisting of 318 grams of ammonium persulfate and 2.5 lbs. of soft water is added. Generally this catalyst solution addition is not necessary. At the end of the exothermic reaction, approximately five hours from the addition of the initial catalyst solution, or when vacuum was no longer needed, the temperature of the resultant polymer/salt slurry was then raised to 173°–177° F. and the vacuum was adjusted to 300 mm of Hg. A catalyst solution consisting of 318 grams of ammonium persulfate and 2.5 pounds of soft water was added and the temperature was held at that level for one hour or until the exothermic reaction had subsided.

The resultant viscous polymer solution is saturated with salt; and if allowed to settle, the salt forms a very viscous cake which cannot be redispersed by normal agitation. In order to obtain complete salt solubility, the product must be diluted to about 30% polymer. The reactor is then cooled and the additional water is added to effect dilution, and a solution homopolymer of DADMAC is recovered. This polymer will contain from 15.0 to 30% polymer and from 4.0 to 12% salt.

EXAMPLE VI

The process of the previous example was repeated using DADMAC prepared in Example IV.

EXAMPLE VII

Using the method outlined above allyl chloride purification monomer synthesis, and polymerizations were conducted. Intrinisic viscosities of the resulting polymer as well as the type of treatment used are indicated in Table I.

TABLE I
PURIFICATION OF ALLYL CHLORIDE

| Run | Treatment | Polymer Intrinisic Viscosity |
|---|---|---|
| A | None | .05 |
| B | Filtered, water wash (Example VI) | 0.31 |
| C | Water wash (Example V) | 0.28 |
| D | Water wash (Example V) | 0.30 |

EXAMPLE VIII

The product of runs A, B C and D of Example VII were tested against a commercially available polyamine having a similar molecular weight in Kaolin settling activity with results being shown in Table II below. Less of the DADMAC polymer prepared by our invention is required than of the commercially available material for an equivalent settling efficiency.

TABLE II

| RUN | ACTIVITY |
|---|---|
| A | None (>>1) |
| B | 0.55 |
| C | 0.66 |
| D | 0.65 |
| Commercially available polyamine | 1.00 |

We claim:
1. A method for the preparation of a solution polymer of diallyl dimethyl ammonium halides, said polymer being prepared from an aqueous monomer solution of diallyl dimethyl ammonium halide containing suspended therein 9.0–20.0% by weight of a water soluble alkali metal halide salt and 25–50% by weight of diallyl dimethyl ammonium halide which comprises the steps of:
  A. Purging said monomer solution;
  B. Heating said monomer solution to a temperature of 120°–180° F.;
  C. Adding to said monomer solution a free radical catalyst;
  D. Polymerizing said monomer solution under free radical forming conditions so as to prepare a polymer of dially dimethyl ammonium chloride in an aqueous solution;

E. Cooling said polymer in aqueous solution while adding water is necessary to solubilize any of said salt contained in said solution.

2. A method for the preparation of a solution polymer of diallyl dimethyl ammonium chloride said polymer being prepared from an aqueous monomer solution of dially dimethyl ammonium chloride containing therein 9.0–20.0% by weight of a suspended water soluble alkali metal halide salt and 25–50% by weight diallyl dimethyl ammonium chloride monomer which comprises the steps of:

A. Purging said monomer solution with an inert gas;
B. Adding to the monomer solution from 0.015–0.05% by weight of a chelating agent based on the weight of dially dimethyl ammonium chloride present in said monomer solution while maintaining a flow of inert gas;
C. Heating said monomer solution with agitation to a temperature of 130°–140° F.;
D. Adding to the monomer solution from 0.75–5.0% by weight based on the weight of diallyl dimethyl ammonium chloride of an inorganic free radical initiator;
E. Maintaining the temperature at 135°–146° F. by applying a vacuum, so as to allow said solution to boil, while adding to the solution water to replace that distilled;
F. Heating said solution to 170°–180° F.;
G. Adding from 0.50–2.50% by weight of an inorganic free radical initiator based on the weight of the diallyl dimethyl ammonium chloride;
H. Maintaining the temperature of Step F for a sufficient period to insure the complete reaction of the diallyl dimethyl ammonium chloride under vacuum while continuously replacing distillate with fresh water;
I. Cooling the resultant solution and diluting said solution with water to a point where all of said alkali metal halide salt is soluble; and then,
J. Recovering a solution homopolymer of diallyl dimethyl ammonium chloride containing 15–30.0% by weight polymer and from 4–12.0% by weight water soluble alkali metal halide salt.

3. The method of claim 1 wherein the chealating agent is the sodium salt of ethylene diamine tetraacetic acid.

4. The method of claim 1 wherein the inorganic free radical initiator is ammonium persulfate.

5. The method of claim 1 wherein the alkali metal halide salt is sodium chloride.

* * * * *

UNITED STATES PATENT AND TRADEMARK OFFICE
CERTIFICATE OF CORRECTION

PATENT NO. : 4,151,202

DATED : April 24, 1979

INVENTOR(S) : Wood E. Hunter et al.

It is certified that error appears in the above-identified patent and that said Letters Patent are hereby corrected as shown below:

Column 9, line 2, "is" should read --- as ---.

Column 10, line 19, "1" should read --- 2 ---.

Column 10, line 19, "chealating" should read --- chelating ---.

Column 10, line 22, "1" should read --- 2 ---.

Column 10, line 24, "1" should read --- 2 ---.

Signed and Sealed this

Thirty-first Day of July 1979

[SEAL]

Attest:

LUTRELLE F. PARKER

Attesting Officer   Acting Commissioner of Patents and Trademarks